(12) United States Patent
Thomas (10) Patent No.: US 7,055,237 B2
(45) Date of Patent: Jun. 6, 2006

(54) METHOD OF FORMING A DRUG ELUTING STENT

(75) Inventor: Richard Thomas, Cloverdale, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 182 days.

(21) Appl. No.: 10/674,299

(22) Filed: Sep. 29, 2003

(65) Prior Publication Data

US 2005/0074545 A1   Apr. 7, 2005

(51) Int. Cl.
   *A61F 2/82*   (2006.01)
(52) U.S. Cl. .......................... 29/458; 29/508; 29/527.2; 623/1.15; 623/1.42; 623/1.46; 427/2.1; 427/2.24; 72/46; 72/47; 72/357; 72/360
(58) Field of Classification Search .............. 29/458, 29/508, 517, 527.2; 623/1.16, 1.2, 1.42, 623/1.43, 1.15, 1.46, 1.47, 1.48; 427/2.1, 427/2.24, 2.25; 72/46, 47, 284, 285, 352, 72/357, 360, 370.25, 470
See application file for complete search history.

(56) References Cited

U.S. PATENT DOCUMENTS

| | | | |
|---|---|---|---|
| 4,739,762 A | 4/1988 | Palmaz | |
| 5,011,494 A | 4/1991 | Von Recum et al. | |
| 5,133,732 A | 7/1992 | Wiktor | |
| 5,292,331 A | 3/1994 | Boneau | |
| 5,421,955 A | 6/1995 | Lau et al. | |
| 5,893,867 A * | 4/1999 | Bagaoisan et al. | 606/198 |
| 5,972,027 A | 10/1999 | Johnson | |
| 6,090,127 A | 7/2000 | Globerman | |
| 6,120,847 A | 9/2000 | Yang et al. | |
| 6,156,373 A | 12/2000 | Zhong et al. | |
| 6,167,605 B1 * | 1/2001 | Morales | 29/282 |
| 6,344,055 B1 * | 2/2002 | Shukov | 623/1.15 |
| 6,695,920 B1 * | 2/2004 | Pacetti et al. | 118/500 |
| 6,702,845 B1 * | 3/2004 | Cully et al. | 623/1.15 |
| 6,702,850 B1 * | 3/2004 | Byun et al. | 623/1.44 |
| 6,726,713 B1 * | 4/2004 | Schaldach et al. | 623/1.11 |
| 2002/0007209 A1 | 1/2002 | Scheerder et al. | |
| 2002/0042645 A1 * | 4/2002 | Shannon | 623/1.13 |
| 2002/0065548 A1 * | 5/2002 | Birdsall et al. | 623/1.15 |
| 2003/0233141 A1 * | 12/2003 | Israel | 623/1.15 |

* cited by examiner

*Primary Examiner*—Marc Jimenez
*Assistant Examiner*—Jermie E. Cozart
(74) *Attorney, Agent, or Firm*—Catherine C. Maresh (57) ABSTRACT

The present invention provides a method of forming a drug eluting stent, the method comprising coupling a stent framework to a mandrel, inserting the mandrel with stent framework into an open die, the die including a forming surface including a plurality of raised indention forming portions; closing the die against the stent framework; pressing the raised indention portions into the stent framework to form indentions in the stent framework; and inserting at least one drug polymer into the indentions formed in the stent framework.

11 Claims, 7 Drawing Sheets

METHOD OF FORMING A DRUG ELUTING STENT

TECHNICAL FIELD

This invention relates generally to biomedical devices that are used for treating vascular conditions. More specifically, the invention relates to a stent assembly that includes delivery openings to deliver a therapeutic agent.

BACKGROUND OF THE INVENTION

Stents are generally cylindrical shaped devices that are radially expandable to hold open a segment of a blood vessel or other anatomical lumen after implantation into the body lumen. Stents have been developed with coatings to deliver drugs or other therapeutic agents.

Various types of stents are in use, including balloon expandable and self-expanding stents. Balloon expandable stents generally are conveyed to the area to be treated on balloon catheters or other expandable devices. For insertion, the stent is positioned in a compressed configuration along the delivery device, for example crimped onto a balloon that is folded or otherwise wrapped about a guide catheter that is part of the delivery device. After the stent is positioned across the lesion, it is expanded by the delivery device, causing the stent diameter to expand. For a self-expanding stent, commonly a sheath is retracted, allowing expansion of the stent.

Stents are used in conjunction with balloon catheters in a variety of medical therapeutic applications including intravascular angioplasty. For example, a balloon catheter device is inflated during PTCA (percutaneous transluminal coronary angioplasty) to dilate a stenotic blood vessel. The stenosis may be the result of a lesion such as a plaque or thrombus. After inflation, the pressurized balloon exerts a compressive force on the lesion thereby increasing the inner diameter of the affected vessel. The increased interior vessel diameter facilitates improved blood flow. Soon after the procedure, however, a significant proportion of treated vessels re-narrow or collapse.

To prevent acute vessel narrowing or collapse, short flexible cylinders, or stents, constructed of metal or various polymers are implanted within the vessel to maintain lumen size. The stents acts as a scaffold to support the lumen in an open position. Various configurations of stents include a cylindrical tube defined by a mesh, interconnected stents or like segments. Some exemplary stents are disclosed in U.S. Pat. No. 5,292,331 to Boneau, U.S. Pat. No. 6,090,127 to Globerman, U.S. Pat. No. 5,133,732 to Wiktor, U.S. Pat. No. 4,739,762 to Palmaz and U.S. Pat. No. 5,421,955 to Lau. Balloon-expandable stents are mounted on a collapsed balloon at a diameter smaller than when the stents are deployed. Stents can also be self-expanding, growing to a final diameter when deployed without mechanical assistance from a balloon or like device.

Stent insertion may cause undesirable reactions such as inflammation, infection, thrombosis, and proliferation of cell growth that occludes the passageway. Stents have been used with coatings to deliver drugs or other therapeutic agents at the site of the stent that may assist in preventing these conditions. In some methods of producing a stent designed to deliver a drug, the drug coating is applied to a stent framework. This may result in the drug being delivered to only those portions of the vessel in direct contact with the stent. The coating can be applied as a liquid containing the drug or other therapeutic agent dispersed in a polymer/solvent matrix. The liquid coating then dries to a solid coating upon the stent. The liquid coating can be applied by dipping or spraying the stent while spinning or shaking the stent to achieve a uniform coating. Combinations of the various application techniques can also be used.

To increase the amount of therapeutic agent that may be deposited on the surface of the stent, the surface of the stent framework can be modified. Modifications may take the form of channels, holes or grooves on the stent surface as well as holes extending through the stent framework. However, placement of these modifications in a consistent manner is difficult leading to inconsistent amounts of drug deposition and elution.

It would be desirable, therefore, to provide a stent having a modified surface for improved drug delivery that would overcome these and other disadvantages.

SUMMARY OF THE INVENTION

One aspect of the present invention provides a method of forming a drug eluting stent, the method comprising coupling a stent framework to a mandrel, inserting the mandrel with stent framework into an open die, the die including a forming surface including a plurality of raised indention forming portions; closing the die against the stent framework; pressing the raised indention portions into the stent framework to form indentions in the stent framework; and inserting at least one drug polymer into the indentions formed in the stent framework.

Another aspect of the invention provides an apparatus for forming a drug eluting stent. The apparatus includes a mandrel, a die set including at least two portions, the at least two portions defining a channel formed through the die set for receiving the mandrel and a plurality of indentation forming portions coupled to a portion of the surface of the channel.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION OF THE PRESENTLY PREFERRED EMBODIMENT

Figure 1:
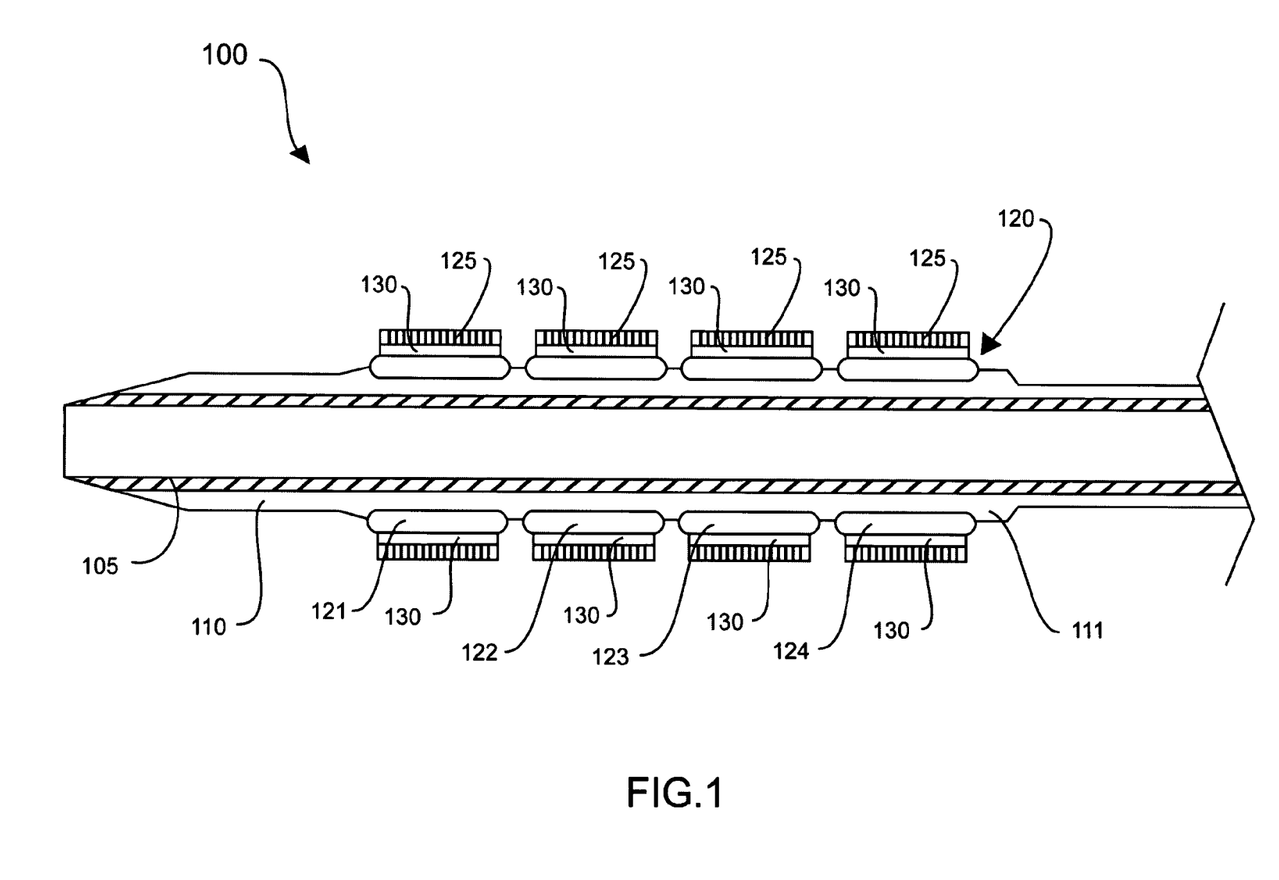
FIG. 1 shows a stent delivery system made in accordance with the present invention.

FIG. 1 shows a stent delivery system made in accordance with the present invention. The stent delivery system 100 includes a catheter 105, a balloon 110 operably attached to the catheter 105, and a stent 120 disposed on the balloon 110. The balloon 110, shown in a collapsed state, may be any variety of balloons capable of expanding the stent 120. The balloon 110 may be manufactured from any sufficiently elastic material such as polyethylene, polyethylene terephthalate (PET), nylon, Pebax® polyether-block co-polyamide polymers, or the like. In one embodiment, the balloon 110 may include retention means 111, such as mechanical or adhesive structures, for retaining the stent 120 until it is deployed. The catheter 105 may be any variety of balloon catheters, such as a PTCA (percutaneous transluminal coronary angioplasty) balloon catheter, capable of supporting a balloon during angioplasty.

The stent 120 may be any variety of implantable prosthetic devices capable of carrying a coating known in the art. In one embodiment, the stent 120 may have a plurality of identical cylindrical stent segments placed end to end. Four stent segments 121, 122, 123, and 124 are shown, and it will be recognized by those skilled in the art that an alternate number of stent segments may be used.

The stent 120 includes at least one cap coating 125, which can be applied to the stent 120 by dipping or spraying the stent 120 with a coating liquid, or applying the coating liquid with a combination of methods. The cap coating 125 can be applied as a liquid polymer/solvent matrix. A therapeutic agent can be incorporated in the cap coating 125, or can be omitted and the cap coating 125 included for its mechanical properties alone. A coating section 130 between the cap coating 125 and the stent 120 is the primary carrier for a therapeutic agent. The cap coating 125 can be applied as a liquid containing the drug or other therapeutic agent dispersed in a polymer/solvent matrix.

The cap coating 125 can be used for a number of purposes, including, but not limited to, a diffusion barrier to control the elution rate of the therapeutic agent from the coating section 130, a protective barrier to prevent damage to the coating section 130, a drug carrier for the same drug as the coating section 130 or a different drug, a lubricating layer to reduce friction between the stent and the balloon of the stent delivery system, or combinations thereof. In one embodiment, the cap coating 125 can be of a single material and uniform thickness to form a concentric cap coating.

Coating section 130 may comprise one or more therapeutic agents dispersed within or encased by a polymeric coating, which are eluted from stent 120 with controlled time delivery after deployment of stent 120 within a body. A therapeutic agent is capable of producing a beneficial effect against one or more conditions including inflammation, coronary restenosis, cardiovascular restenosis, angiographic restenosis, arteriosclerosis, hyperplasia, and other diseases and conditions. For example, the therapeutic agent can be selected to inhibit or prevent vascular restenosis, a condition corresponding to a narrowing or constriction of the diameter of the bodily lumen where the stent is placed. Coating section 130 may comprise, for example, an antirestenotic drug, an antisense agent, an antineoplastic agent, an antiproliferative agent, an antithrombogenic agent, an anticoagulant, an antiplatelet agent, an antibiotic, an antiinflammatory agent, a steroid, a gene therapy agent, an organic drug, a pharmaceutical compound, a recombinant DNA product, a recombinant RNA product, a collagen, a collagenic derivative, a protein, a protein analog, a saccharide, a saccharide derivative, a bioactive agent, a pharmaceutical drug, a therapeutic substance, or combinations thereof. The elution rates of the therapeutic agents into the body and the tissue bed surrounding the stent framework are based on the constituency and thickness of coating section 130, the nature and concentration of the therapeutic agents, the thickness and composition of cap coating 125, and other factors.

The cap coating 125 and coating section 130 can be a polymer including, but not limited to, urethane, polyester, epoxy, polycaprolactone (PCL), polymethylmethacrylate (PMMA), PEVA, PBMA, PHEMA, PEVAc, PVAc, Poly N-Vinyl pyrrolidone, Poly (ethylene-vinyl alcohol), combinations of the above, and the like. Suitable solvents that can be used to form the liquid coating include, but are not limited to, acetone, ethyl acetate, tetrahydrofuran (THF), chloroform, N-methylpyrrolidone (NMP), combinations of the above, and the like. Suitable therapeutic agents include, but are not limited to, antiangiogenesis agents, antiendothelin agents, antimitogenic factors, antioxidants, antiplatelet agents, antiproliferative agents, antisense oligonucleotides, antithrombogenic agents, calcium channel blockers, clot dissolving enzymes, growth factors, growth factor inhibitors, nitrates, nitric oxide releasing agents, vasodilators, virus-mediated gene transfer agents, agents having a desirable therapeutic application, combinations of the above, and the like. Specific example of therapeutic agents include abciximab, angiopeptin, colchicine, eptifibatide, heparin, hirudin, lovastatin, methotrexate, streptokinase, taxol, ticlopidine, tissue plasminogen activator, trapidil, urokinase, and growth factors VEGF, TGF-beta, IGF, PDGF, and FGF.

The cap coating 125 and coating section 130 are merely exemplary, and it should be recognized that other coating configurations, such as multiple coating layers, are possible. Although the cap coating 125 and the coating section 130 are shown schematically on the outer circumference of the stent 120, the cap coating 125 and the coating section 130 can coat the whole stent 120, both inside and outside, and around the cross section of individual stent wires. In another embodiment, the coating section 130 can be present on a portion of the stent 120 without a cap coating 125 on that same portion.

The different coatings can be made of the same material or different materials, and can contain the same therapeutic agents or different therapeutic agents. The coatings can be applied as a liquid polymer/solvent matrix. The liquid coating can be applied to the stent 120 by pad printing, inkjet printing, rolling, painting, spraying, micro-spraying, dipping, wiping, electrostatic deposition, vapor deposition, epitaxial growth, combinations thereof, and other methods as will be appreciated by those skilled in the art.

Figure 2:
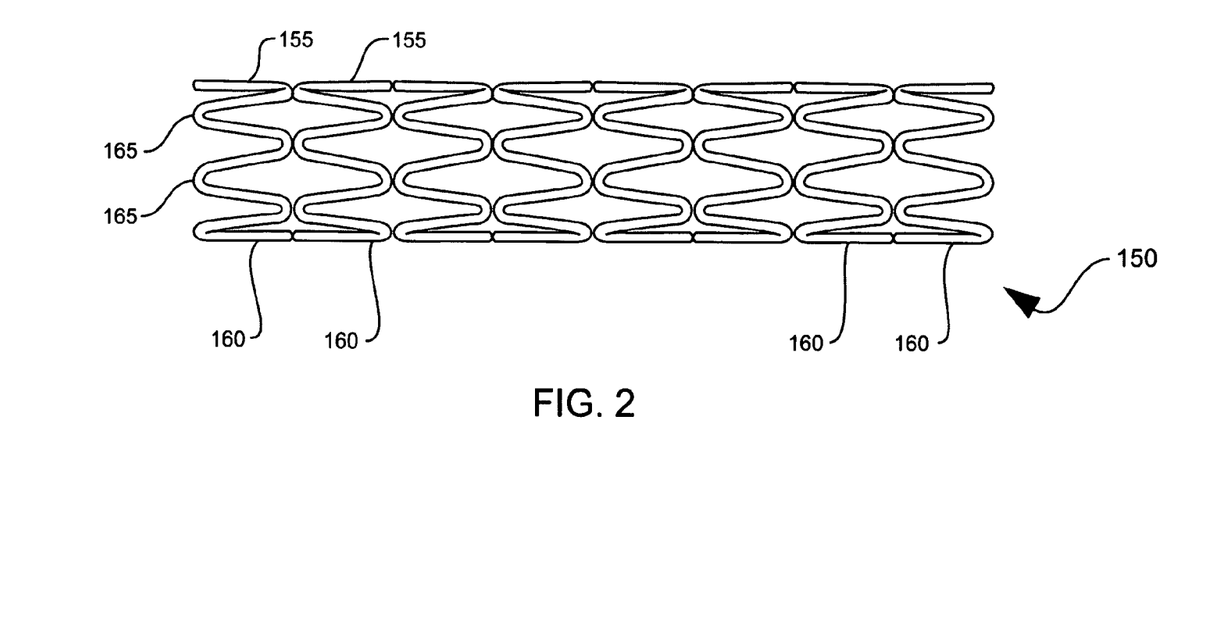
FIG. 2 shows a coated stent made in accordance with the present invention.

FIG. 2 is a side view of an illustrative embodiment of a stent used for forming a stent embodying the principles of the present invention. The stent 150 comprises a number of segments 160 each of which is made of an endless metal loop that has been bent into a plurality of straight sections or struts 155 that are integrally joined by discrete axial turns, or crowns 165. Axially adjacent segments 160 may be joined to one another at one or more of their crowns 165. These connections may be made by welding, soldering, adhesive bonding, mechanical fastening, or in any other suitable manner. The pattern of the segments 160 can be W-shaped or can be a more complex shape with the elements of one segment continuing into the adjacent segment. Each segment 160 may have more undulations than are shown in FIG. 2, but the simplified depictions shown herein will be sufficient to illustrate the present invention. The stent 150 can be installed in the stent delivery system of FIG. 1 for implantation in a body lumen.

Referring to FIG. 2, the stent 150 is conventional to stents generally and can be made of a wide variety of medical implantable materials, such as stainless steel (particularly 316-L stainless steel or 316LS), cobalt base alloys, nitinol, tantalum, ceramic, nickel, titanium, aluminum, polymeric materials, tantalum, MP35N, titanium ASTM F63-83 Grade 1, niobium, high carat gold K 19–22, and combinations thereof. The stent 150 can be formed through various methods as well. The stent 150 can be welded, laser cut, molded, or consist of filaments or fibers which are wound or braided together in order to form a continuous structure. Although segments 160 may or may not be made of what would be regarded in some other arts as wire, the material of segments 160 is generally wire-like, and so the term "wire" is sometimes used herein to refer to such stent material. Depending on the material and design, the stent can be self-expanding, or be expanded by a balloon or some other device. The cap coating and coating section can be on the surface of the segments 160.

Figures 3, 6:
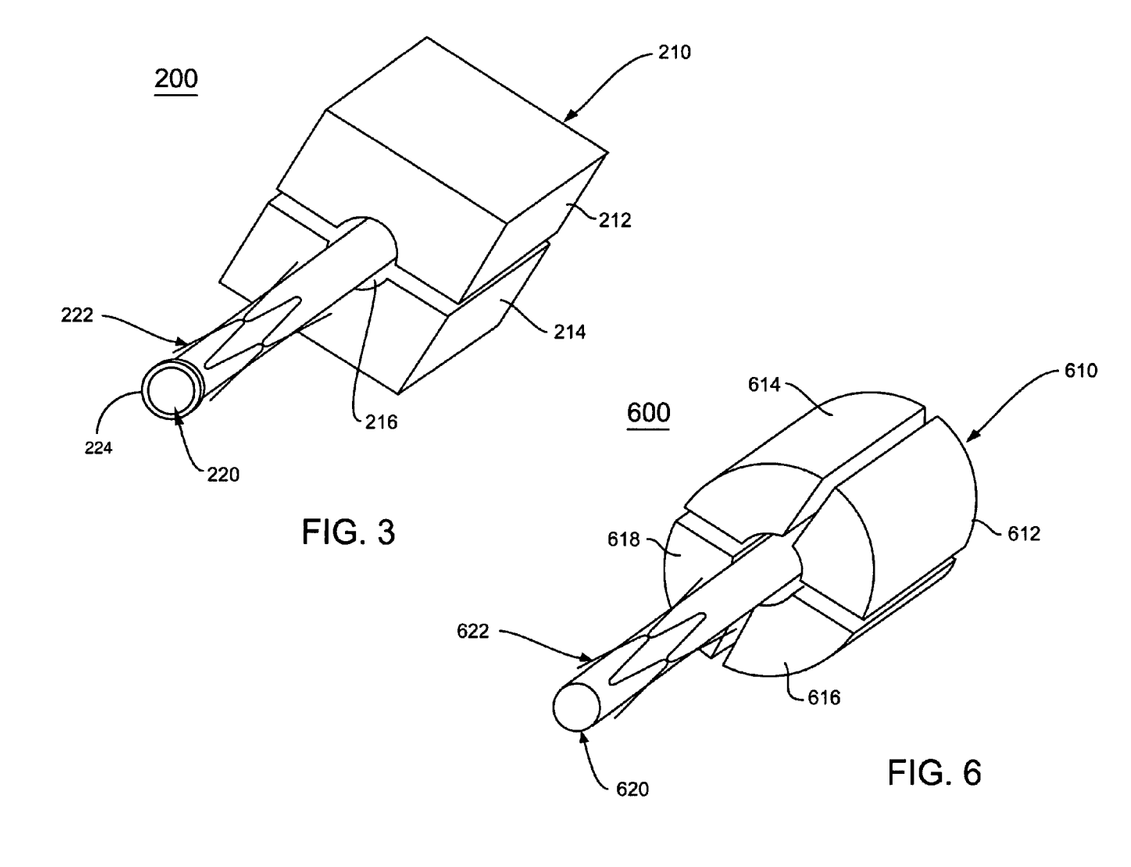
FIG. 3 shows a stent made in accordance with the present invention positioned on one embodiment of a swaging apparatus.
FIG. 6 shows a stent made in accordance with the present invention positioned on another embodiment of a swaging apparatus.
Figure 4:
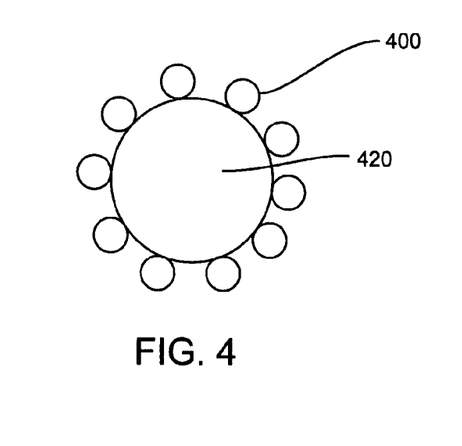
FIG. 4 shows a cross section of a stent before swaging.
Figure 5:
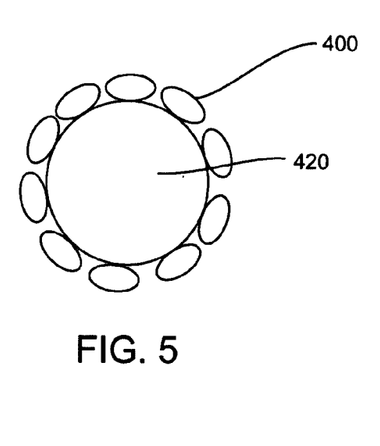
FIG. 5 shows a cross section of a stent after swaging.

Referring now to FIGS. 3 to 5, the manufacture of the drug eluting stent according to the present invention begins with a conventional stent such as the stent illustrated in FIG. 2. After the stent is formed, the stent undergoes a swaging (profiling) process. This process is described in commonly owned co-pending U.S. patent application Ser. No. 10/029,553 titled "Profiled Stent and Method of Manufacture" by Matthew J. Birdsall, the entirety of which is incorporated by reference. During this process, the profile of the stent struts are altered as best illustrated in FIGS. 4 and 5. FIG. 4 shows a cross section through stent struts 400 of a closed stent positioned on mandrel 420 before the profiling process. The cross section of the stent struts 400 before the process is of a generally circular nature. FIG. 5 shows the same closed stent section after undergoing the profiling process. After the procedure, the cross section of the stent strut 400 is of a generally ellipto-rectangular nature.

FIG. 3 illustrates the rotary swaging device 200 for profiling a stent 222. The swaging device 200 includes a die set 210 and a swaging mandrel 220. The die set 210 illustrated includes two parts, a top portion 212 and a bottom portion 214. The stent 222 is disposed upon the swaging mandrel 220 before insertion into the swaging die set 210. The swaging mandrel 220 may include a collar portion 224 to prevent the stent 222 from sliding off the mandrel 220 during the profiling process.

The top portion 212 and a bottom portion 214 each have a semicircular channel 216 that is polished to a mirror finish. This polished surface aids in removing any defects on the stent surface and smoothing the stent surface. In the closed position, the semicircular channel 216 has a diameter that is less than that of the stent 222 positioned on the mandrel 220. In one embodiment, the diameter of the semicircular channel 216 in the fully closed position is approximately 0.0002–0.0015 inch less than that of the stent positioned on the mandrel.

Figure 7:
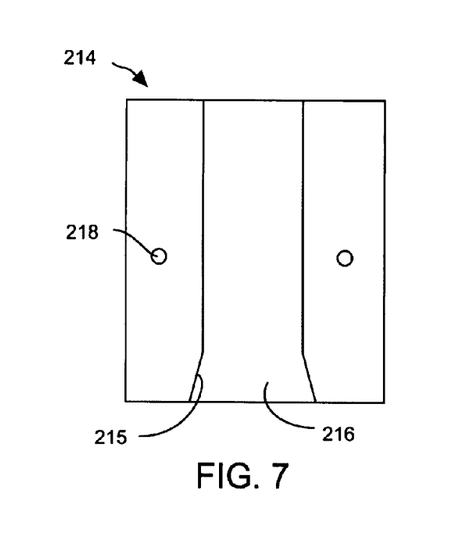
FIG. 7 shows a top view of a bottom portion of a swaging apparatus used in accordance with the present invention.

FIG. 7 illustrates the inside face of bottom portion 214. The semicircular channel 216 is slightly tapered 215 toward the inside of the die in a funnel like manner to facilitate the entry of the stent into the die and to accommodate the increased diameter of the stent before profiling as compared to the stent diameter after profiling. FIG. 7 also illustrates the connection means for operably connecting top portion 212 to a bottom portion 214. Top portion 212 and a bottom portion 214 are connected via a pair of springs (not shown) that are each disposed in spring seats 218. The springs aid in the translation of the top portion 212 and a bottom portion 214 relative to each other during the profiling process.

Returning now to FIG. 3, during the swaging process, the stent is swaged by passing the stent 222 and swage mandrel 220 through the rotating die set 210 while the die set is repeatedly opened and closed. The closed die forces the stent to conform to the annular space defined between the mandrel 220 and the closed die set 210. As stated above, in the fully closed state, the diameter of the swage die set channel is less than the outer diameter of the stent positioned on the mandrel. The effect is a reduction of the stent strut thickness. Furthermore, the profile of the stent is changed as described above in relation to FIGS. 4 and 5.

In a preferred embodiment, the entire stent is profiled. The stent however could be preferentially profiled by profiling only the struts 155 or only the crowns 165 where most of the stress occurs in the instance of a multi-section stent, or by selectively profiling one or more stent sections.

Other methods for swaging a stent are available. In one preferred embodiment of the present invention, a stent is profiled by swaging the stent by either using a swaging machine or by using a collet. In another embodiment, the stent is profiled using a roller method. In yet another embodiment, the stent is profiled using a sizing tube and forming tool. A non-rotary swage machine is also suitable.

FIG. 6 is a block diagram illustrating another embodiment of a swaging assembly 600. FIG. 6 shows the profiling of stent 622 using a collet 610. Similar to the rotary swage machine 200, a conventional stent is placed over mandrel 620 which is in turn placed into the collet 610. Collet 610 comprises four wedge shaped portions 612, 614, 616, 618 that define a polished channel similar to that of swaging die set 210. Collet 610 is closed, forcing the stent to conform to the annular space defined between the mandrel 620 and the closed collect 610.

Figure 8:
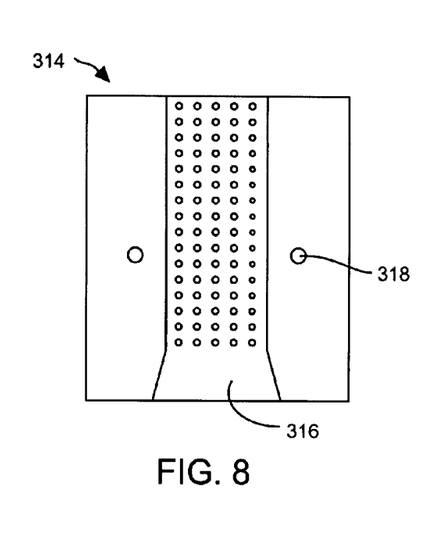
FIG. 8 shows a top view of a bottom portion of a swaging apparatus having a dimple forming surface used in accordance with the present invention.
Figure 9:
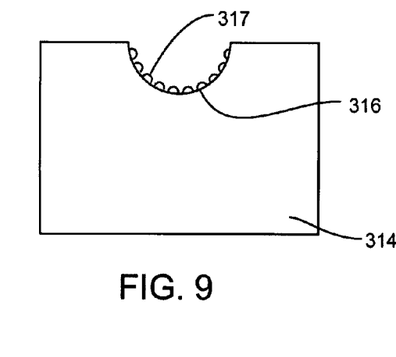
FIG. 9 shows a cross section of the bottom portion illustrated in FIG. 8.
Figure 10:
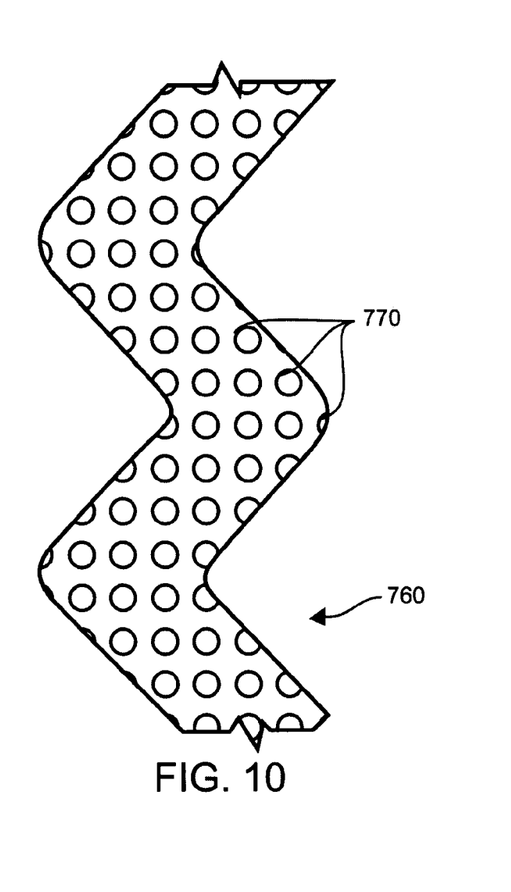
FIG. 10 shows a detailed section of a dimpled stent segment made in accordance with the present invention.

Referring now to FIGS. 8–10, an apparatus for improving the drug loading capacity of a profiled stent is illustrated in accordance with the present invention. In order to improve the drug loading capacity of a stent, the present invention modifies the surface of a stent. The modification is in the form of providing a plurality of dimples, or indentations, to the surface of the stent. This is accomplished by altering the channel surface of the top and bottom portions of a die set similar to that illustrated in FIG. 3.

FIG. 8 illustrates the top view of the bottom portion 314 and FIG. 9 illustrates a cross section of the bottom portion 314 of a die set similar to the die set 210 used in the profiling process described above. However, the forming surface of the semicircular channel 316 of the bottom portion 314 and top portion (not shown) has been modified to include a plurality of raised indention forming portions 317. The indention forming portions 317 form dimples on the surface of the stent framework when the die set is closed upon a stent positioned on a mandrel that has been inserted into the modified die assembly. The die set can be repeatedly opened, the mandrel with the stent repositioned, and the die set closed in order that the surface of the stent is covered with indentations due to pressing the indentation forming portions onto the surface of the stent. FIG. 10 illustrates a portion of a stent having undergone the dimple forming process. Stent segment 760 is shown having a plurality of indentation or dimples 770.

Those of ordinary skill in the art will recognize that the pattern of dimples may be varied. The number and size of the indention forming portions 317 may be varied to increase or decrease the amount of therapeutic agent coated on the stent. Those of ordinary skill in the art will recognize that the shape of the indention forming portions 317 may also be varied depending on the application.

The indention forming portions 317 on the forming surface of the semicircular channel may be produced by several methods. For example, the indention forming portions 317 may be welded onto the surface of the channel. Other methods include, but are not limited to, photochemical etching, lithography, bead blasting and electrodeposition.

Figure 11:
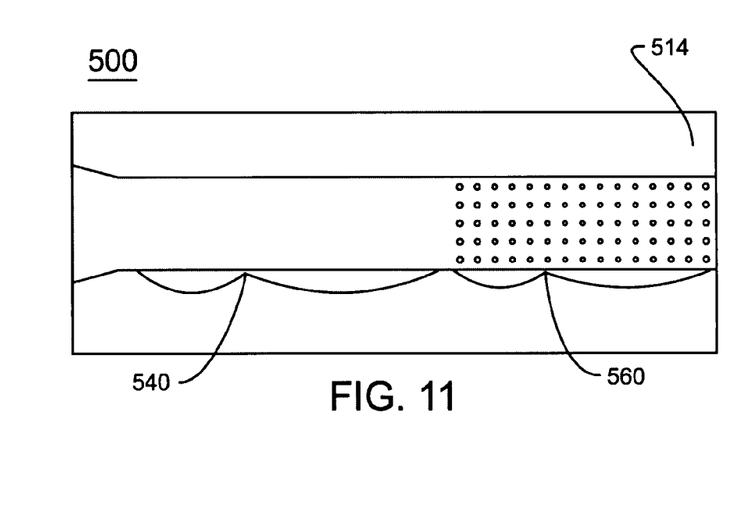
FIG. 11 shows yet another alternate embodiment of a top view of a bottom portion of a swaging apparatus having a polished portion and a dimple forming portion made in accordance with the present invention.

FIG. 11 illustrates another embodiment 500 of the die set in accordance with the present invention. In the embodiment illustrated in FIGS. 8 and 9, the stent is profiled in one die set and moved to another die set for dimpling. In the embodiment illustrated in FIG. 11 a single die set is used. FIG. 11 illustrates the bottom portion 514 of a two piece die set having a mirror finished portion 540 for profiling the stent and an indentation forming portion 560 for forming the dimples on the stent.

Figure 12:
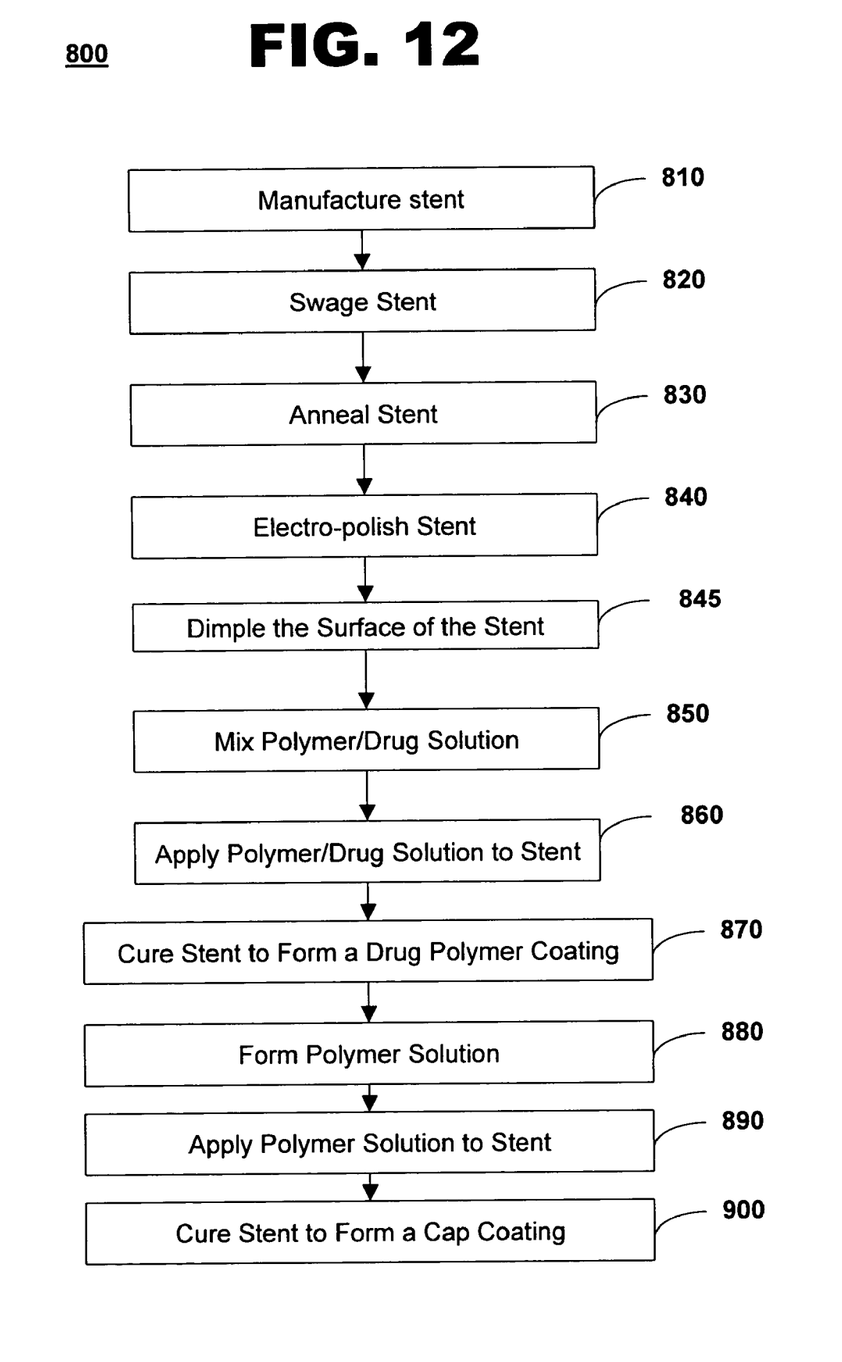
FIG. 12 is a flow chart illustrating a method of manufacturing a stent in accordance with the present invention.

FIG. 12 is a flow chart depicting the process 800 of producing a coated stent in accordance with the present invention. The process 800 begins by manufacturing a conventional stent, (Step 810). The particular type of stent manufactured may include self-expandable stents or balloon-expandable stents, and tubular-slotted stents or wire-like stents as described above.

After the stent is manufactured, the stent is swaged in order to provide a profiled stent of a desired thickness (Step 820). After swaging, the profiled stent is annealed (Step 830) to soften and de-stress the material comprising the stent. After annealing, the stent is electro-polished (Step 840). The stent is then inserted into an indentation forming die set to dimple the surface of the stent (Step 845). The stent may be repositioned as often as necessary to provide the desired number and pattern of individual dimples.

The dimpled stent may then be coated (Steps 850 to 900). A first polymer and drug (or other therapeutic agent) are mixed with a first solvent to form a polymer/drug solution (Step 850). The polymer/drug solution is applied to the stent and inserted into the indentations on the dimpled surface in a coating layer (Step 860) and the coating layer cured to form a drug polymer coating (Step 870). A second polymer is mixed with a second solvent to form a polymer solution (Step 880). The polymer solution is applied to the drug polymer coating in a cap layer (Step 890) and the cap layer cured to form a cap coating (Step 900).

If the stent is self expanding, then the stent can be placed on a catheter. If the stent is a balloon inflatable stent, then the stent is crimped onto a balloon catheter for subsequent insertion into a lumen.

Those skilled in the art will appreciate that the method of manufacturing can be varied for the materials used and the results desired. For certain polymer/drug solutions and polymer solutions, the curing step can be omitted or can be a simple drying process. In another embodiment, the first polymer and first solvent can be the same combination as the second polymer and second solvent. In yet another embodiment, the polymer solution can also contain a drug or other therapeutic agent.

Figure 13:
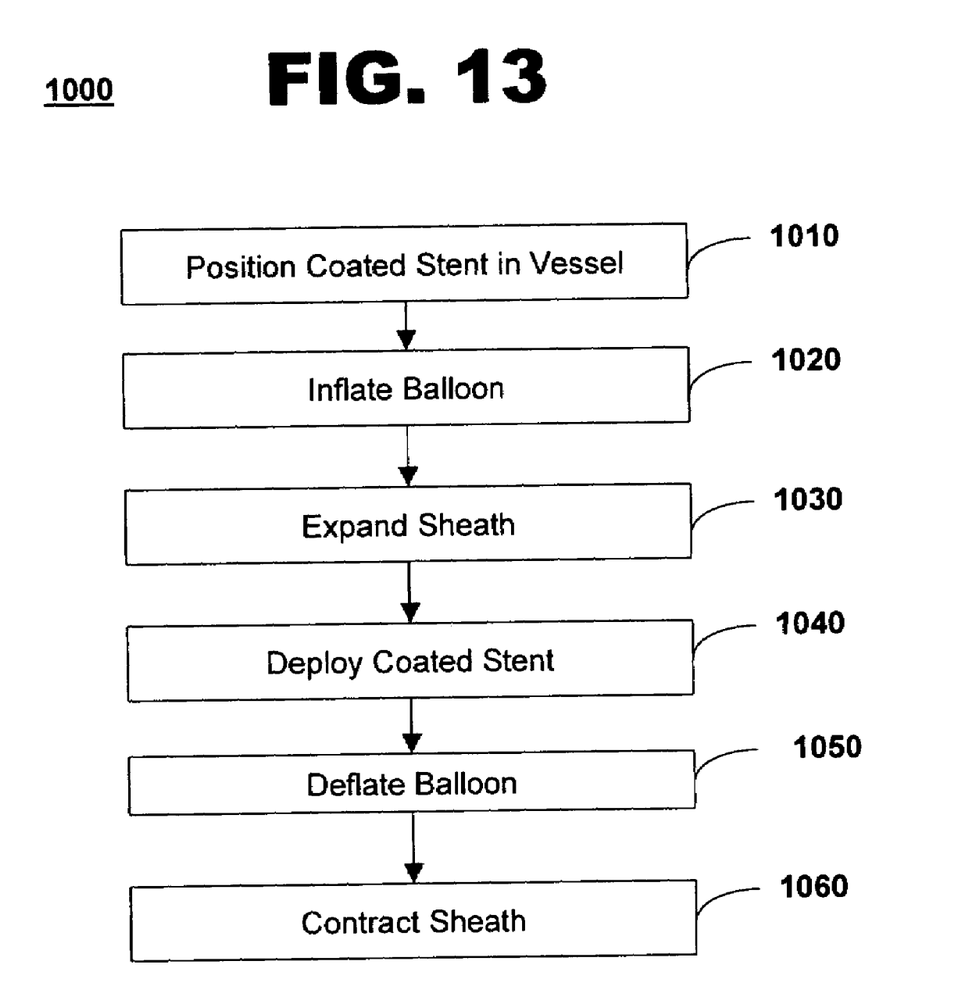
FIG. 13 is a flow chart illustrating a method of using the stent manufactured in accordance with the present invention.

FIG. 13 shows a flow diagram of a method for deploying a drug-polymer coated stent in a vessel, in accordance with one embodiment of the present invention at 1000. Coated stent deployment method 1000 includes various steps to deploy a drug-polymer coated stent in a vessel in a body.

A drug-polymer coated stent is positioned in a vessel in the body, (Step 1010). The vessel may be located in one of many vessels within the cardiovascular system, or in other vascular systems within the body such as the cerebrovascular system, the urinogenital system, biliary conduits, abdominal passageways, or peripheral vasculature. A catheter coupled to the drug-polymer coated stent in conjunction with a guide wire is inserted into one of the vessels of the body such as the femoral artery, and the coated stent is guided through one or more vessels into a directed location within the body. The coated stent position may be monitored, for example, using radiopaque markers or radiopaque fluid with associated x-ray imaging systems. The guide wire and catheter are manually manipulated through the vascular system to the desired location for stent deployment.

The balloon is inflated, (Step 1020). The balloon is filled with a liquid such as a contrast fluid that is fluidly coupled through the catheter from a source external to the body. As pressure is applied to the fluid, the balloon enlarges. As the balloon expands, a coated stent surrounding the balloon expands.

The coated stent is deployed, (Step 1040). The coated stent is deployed with the balloon. The coated stent is enlarged and is secured against the tissue bed of the vascular wall. The size of the deployed stent is determined in part by the maximum pressure applied to the fluid when inflating the balloon.

The balloon is deflated after the coated stent is deployed, (Step 1050). The pressure applied to the interior of the balloon is reduced and the coated stent separates from the balloon. Liquid in the balloon may be pumped out, collapsing the balloon even further. The balloon and catheter are then withdrawn from the vessel.

It is important to note that FIGS. 1–13 illustrate specific applications and embodiments of the present invention, and is not intended to limit the scope of the present disclosure or claims to that which is presented therein. For example, the cap coating and coating layer can be applied in a variety of conventional ways, including painting, spraying, dipping, wiping, electrostatic deposition, vapor deposition, epitaxial growth, combinations thereof, and other methods known to those of ordinary skill in the art. The means of applying the liquid coating, such as spray nozzles or pads, can be moved in various paths relative to the stent to achieve particular patterns and thickness variations. Upon reading the specification and reviewing the drawings hereof, it will become immediately obvious to those skilled in the art that myriad other embodiments of the present invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

I claim:

1. A method of forming a drug eluting stent, the method comprising:
   coupling a stent framework to a mandrel;
   inserting the mandrel with stent framework into an open die set, the die set including a forming surface including a plurality of raised indention forming portions;
   closing the die set against the stent framework;
   pressing the raised indention portions into the stent framework to form indentions in the stent framework; and
   inserting at least one drug polymer into the indentions formed in the stent framework.

2. The method of claim 1 further comprising:
   reopening the die set and repositioning the stent framework within the reopened die set, reclosing the die set and pressing the raised indention forming portions into the stent framework.

3. The method of claim 2 wherein the repositioning comprises rotating the mandrel with stent within the reopened die set.

4. The method of claim 1 further comprising:
   reopening the die set;
   rotating the die set in relation to the stent on the mandrel; and
   reclosing the die set to press the raised indention portions into a different position on the stent framework.

5. The method of claim 1 further comprising:
   coupling a collar to the mandrel adjacent one end of the stent framework.

6. The method of claim 1 wherein the raised indention forming portions are formed by a process selected from the group consisting of: welding, photo chemical etching, lithography, bead blasting and electrodeposition.

7. The method of claim 1 wherein inserting at least one drug polymer into the indentions comprises applying a drug polymer solution onto the stent and curing the stent to form a drug polymer coating.

8. The method of claim 7 further comprising:
   applying a polymer solution to the drug polymer coated stent; and
   curing the stent to form a polymer cap coating.

9. The method of claim 8 wherein the cap coating comprises a polymer selected from the group consisting of a silicone-urethane copolymer, a polyurethane, a phenoxy, ethylene vinyl acetate, polycaprolactone, poly(lactide-co-glycolide), polylactide, polysulfone, elastin, fibrin, collagen, chondroitin sulfate, a biocompatible polymer, a biostable polymer, a biodegradable polymer, and a combination thereof.

10. The method of claim 7 wherein the drug polymer solution contains at least one therapeutic agent.

11. The method of claim 10 wherein the therapeutic agent is selected from the group consisting of an antisense agent, an antineoplastic agent, an antiproliferative agent, an antithrombogenic agent, an anticoagulant, an antiplatelet agent, an antibiotic, an anti-inflammatory agent, a therapeutic peptide, a gene therapy agent, a therapeutic substance, an organic drug, a pharmaceutical compound, a recombinant DNA product, a recombinant RNA product, a collagen, a collagenic derivative, a protein, a protein analog, a saccharide, a saccharide derivative, and a combination thereof.

* * * * *